United States Patent [19]

Arraudeau et al.

[11] Patent Number: 5,053,220
[45] Date of Patent: Oct. 1, 1991

[54] MASCARA COMPOSITION BASED ON WAXES AND KERATIN DERIVATIVES

[75] Inventors: Jean-Pierre Arraudeau; Jeanne Patraud, both of Paris; Didier Gagnebien, Levallois-Perret; Gérard Lang, Saint-Gratien; Alain Malaval, Marly La Ville, all of France

[73] Assignee: L'Oreal, Paris, France

[21] Appl. No.: 368,718

[22] Filed: Jun. 21, 1989

Related U.S. Application Data

[63] Continuation-in-part of Ser. No. 799,496, Nov. 19, 1985, abandoned.

[30] Foreign Application Priority Data

Nov. 20, 1984 [FR] France ................... 84 17661

[51] Int. Cl.$^5$ ...................... A61K 7/021; A61K 7/035
[52] U.S. Cl. ......................................... 424/63; 424/69; 424/401; 424/502
[58] Field of Search ................... 424/63, 69, 401, 502; 514/2, 21, 844, 845

[56] References Cited

U.S. PATENT DOCUMENTS 4,504,644  3/1985  Lang et al. ................... 527/201

FOREIGN PATENT DOCUMENTS 2529214 12/1983 France .
144209   9/1982 Japan .
2147807  5/1985 United Kingdom .
2167301  5/1986 United Kingdom .

Primary Examiner—John B. Maples
Attorney, Agent, or Firm—Cushman, Darby & Cushman

[57] ABSTRACT

These wax-based mascara compositions have cosmetic properties which are improved by the presence, in combination with the waxes, of keratin sulphonic derivatives of formula

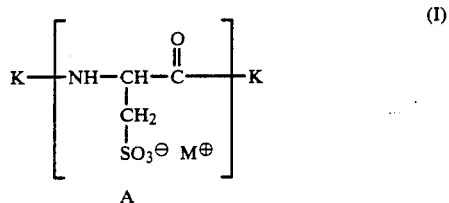

in which formula K denotes the keratin residue, and M+ denotes H+, a cation derived from an alkali metal or magnesium, or $N^+(R)_4$, the radicals R being identical or different and each denoting H or an alkyl or hydroxyalkyl radical containing at most 4 carbon atoms, the unit A denoting from 3 to 15% by weight of the keratin derivative and being the only modified unit in the protein chain of the keratin. The derivatives of formula (I) act both as a cohesion agent and a thickener, enabling a sheathing to be produced on the eyelashes with immediate adhesion and with a flexible film-forming effect.

27 Claims, No Drawings

MASCARA COMPOSITION BASED ON WAXES AND KERATIN DERIVATIVES

This is a continuation-in-part of application Ser. No. 06/799,496, filed Nov. 19, 1985, now abandoned.

The present invention relates to an eyelash make-up composition, the properties of which are improved by the presence of particular keratin derivatives, in combination with the waxes conventionally used in composition of this kind.

In general, cosmetic compositions intended for making-up eyelashes, also known as mascaras, are wax-based, as indicated above. However, it has been noted that when waxes alone are employed the resultant mascara compositions lead to the formation of a nonhomogeneous film on the eyelashes, which is seen as the formation of brittle flakes immediately after drying.

Attempts have been made to overcome this disadvantage by using, together with the waxes, a thickening agent such as hydroxyethylcellulose, the function of which is to ensure the homogeneity of the film on the eyelashes, resulting in uniform make-up. However, the make-up obtained with a product of this kind is characterized by poor lengthening of the eyelashes, and by a stability with time which, while improved relative to the earlier compositions, nevertheless results in the appearance of flakes after a few hours.

A "cohesion agent", such as rosin or its derivatives, has also been used together with the combination of wax and thickener. Mascaras based on a combination of waxes and anionic cationic polymers are also known. These make-ups result in the eyelashes being perfectly sheathed and markedly increase the lengthening properties. In addition, they contribute a degree of "plasticization" of the film on the eyelashes, thus contributing an improved stability with time. Unfortunately, these make-ups require a certain time to apply so that perfect sheathing of the eyelashes is produced.

It appears, as a result, that the present state of the art does not offer any adjuvant for the waxes constituting the mascaras, which has the characteristic of rendering the make-up quick and uniform and that of giving to this make-up a marked lengthening of the eyelashes, together with good stability with time.

The applicants have now found that particular keratin derivatives, when added to wax-based mascaras, surprisingly improve the cosmetic qualities of these mascaras. It was not at all obvious that, when added to the eyelash make-up compositions, they act both as a cohesion agent and a thickener, enabling a sheathing to be produced on the eyelashes with immediate adhesion and with a flexible film-forming effect. Eyelash make-up compositions produced in this way can be very quickly applied to the eyelashes; they provide a substantial lengthening of the eyelashes; and they exhibit good behavior characteristics. The keratin derivatives are obtained, in a known manner, by oxidation of the disulphide in the cystine groups in various keratins; they are water-soluble compounds with a high molecular weight and a high sulphur content. From Japanese Patents Nos. 144,211/1982 and 144,029/1982, these keratin derivatives are known to contribute properties of interest, especially moisture retention and a cool feeling on the skin, to protective creams or lotions for the skin and to cosmetic sticks, respectively, but they have never been described as giving the make-up properties stated above.

The subject of the present invention is consequently an eyelash make-up composition containing an effective quantity of at least one wax, in the presence of a cosmetically acceptable carrier, characterized in that it contains, in combination with the wax(es), an effective quantity of at least one keratin derivative corresponding to the following general formula:

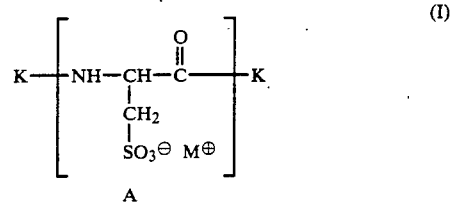

in which formula:

K denotes the keratin residue;

$M^\oplus$ denotes $H^\oplus$, a cation derived from an alkali metal or magnesium or $N^\oplus(R)_4$, in which formula the radicals R are identical or different and denote a hydrogen atom or an alkyl or hydroxyalkyl radical containing at most 4 carbon atoms, the unit A denoting from 3 to 15% by weight of the keratin derivative, the unit A being the only modified unit in the protein chain of the keratin.

The keratin from which the keratin derivative of the formula (I) is prepared may originate from a substance taken from the group consisting of hair, wool, hooves, horn, skin, fur, silk and feathers.

The modified keratins of formula (I) are prepared by oxidation of all or some of the disulphide linkages in the cystine groups in keratin so as to produce cysteic acid groups, this oxidation being, or not being, followed by a conversion of the $-SO_3H$ acid groups to salts. The oxidation is advantageously carried out in an acid medium by means of an oxidizing agent such as hydrogen peroxide or a peracid.

The keratin derivatives are present in the compositions according to the invention in a weight proportion which is generally between 0.1 and 40% relative to the total weight of the composition and advantageously have a molecular weight of between 10,000 and approximately 100,000.

As a general rule, the waxes chosen have a melting point between 60° and 100° C. and a needle penetration, as measured according to the American standard ASTM D5 or according to the French standard NFT 004, of 3 to 40 at 25° C. The principle of the measurement of the needle penetration according to the standards ASTM D5 and NFT 004 consists in measuring the depth, expressed in tenths of a millimeter, to which a standard needle (weighing 2.5 g and placed in a needle holder weighing 47.5 g, i.e. a total of 50 g) penetrates when placed on the wax for 5 seconds.

The waxes employed according to the invention are chosen from animal waxes, plant waxes, mineral waxes, synthetic waxes and the various fractions of natural waxes, all these waxes having the two characteristics, i.e. melting points and needle penetration, indicated above.

Among the animal waxes, there may be mentioned beeswaxes, lanolin waxes and Chinese insect waxes.

Among the plant waxes there may be mentioned carnauba, candelilla and ouricury waxes, cork fiber waxes, sugar cane waxes and Japan waxes.

Among the mineral waxes there may be mentioned, especially, paraffins, microcrystalline waxes, montan waxes and ozokerites.

In the case of synthetic waxes, there may be mentioned, especially, polyethylene waxes, the waxes produced by the Fischer-Tropsch synthesis, and waxy copolymers, as well as their esters.

These waxes are well known in the state of the art. According to the invention, the wax(es) is (or are) present in the mascara composition in proportions of between 2 and 40% by weight relative to the total weight of the composition.

The waxes which can be employed according to the present invention are preferably solid and rigid at a temperature below 50° C.

According to another characteristic of the mascara compositions according to the present invention, the weight ratio of the quantity of keratin derivative(s) employed to the quantity of wax(es) employed is between 0.01 and 1.

The mascara compositions according to the present invention may contain pigments, in addition to the keratin derivatives and the waxes. By virtue of the presence of the above-mentioned keratin derivatives, goods distribution of these pigments in the compositions is obtained, together with an improvement in their attachment to the eyelashes.

The pigments which can be employed in accordance with the invention are chosen from inorganic pigments, organic pigments, and pearlescent pigments.

As examples of inorganic pigments, there may be mentioned titanium dioxide (rutile or anatase), optionally surface-treated and coded in the Color Index under the reference CI 77,891, the black, yellow, red and brown iron oxides, coded under references CI 77,499, 77,492 and, 77,491, manganese violet (CI 77,742), ultramarine blue (CI 77,007), chromium oxide (CI 77,288), chromium hydrate (CI 77,289), and ferric blue (CI 77,510).

The organic pigments are chosen, in particular, from the following pigments: D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10, (CI 45,425), D&C Yellow No. 6 (CI 15,985), D&C Red No. 30 (CI 73,360), D&C Red No. 3 (CI 45,430) and the lakes based on Cochineal Carmine (CI 75,570).

The pearlescent pigments may be chosen from the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride.

When employed, the pigments are present in proportions of 3 to 20% by weight relative to the total weight of the composition, depending on the color and the intensity of the color which it is intended to produce.

The compositions according to the present invention may be presented particularly in the form of oil-in-water or water-in-oil emulsions or in the form of suspensions in a solvent medium or alternatively in dry solid or paste form. The procedures for the preparation of these various kinds of compositions are well known to the person skilled in the art.

When employed in emulsion form, the compositions may contain surface-active agents which ar well known in the state of the art.

A particularly preferred embodiment consists in preparing anionic or nonionic emulsions by using anionic or nonionic surface-active agents in proportions which are preferably between 2 and 30% by weight relative to the total weight of the composition.

Among the anionic surface-active agents which may be used by themselves or mixed, there may be mentioned, in particular, the alkali metal salts, the ammonium salts, the amine salts or the amino-alcohol salts of the following compounds:

alkylsulphates, alkyl ether sulphates, alkylamidosulphates and ether sulphates, alkylaryl polyether sulphates and monoglyceride sulphates, alkylsulphonates, alkylamide sulphonates, alkylarylsulphonates, α-olefin sulphonates and paraffin sulphonates, alkylsulphosuccinates, alkyl ether sulphosuccinates, and alkylamidosulphosuccinates, alkylsulphosuccinamates, alkylsulphoacetates, alkylpolyglycerol carboxylates, alkyl phosphates/alkyl ether phosphates, and alkylsarcosinates, alkylpolypeptidates, alkylamidopolypeptidates, alkylisethionates, and alkyltaurates.

The alkyl radical in all these compounds generally denotes a chain containing 12 to 18 carbon atoms.

Other anionic surface-active agents consist of salts of fatty acids such as oleic, ricinoleic, palmitic and stearic acids, copra oil acids or hydrogenated copra oil acids and especially amine salts such as amine stearates.

There may also be mentioned:
the acyl lactylates in which the acyl radical contains from 8 to 20 carbon atoms, and
the polyglycol ether carboxylic acids corresponding to the formula $$Alk-(OCH_2-CH_2)_n-OCH_2-COOH$$

in acid or salt form, in which the substituent Alk corresponds to a linear chain containing from 12 to 18 carbon atoms and in which n is an integer from 5 to 15.

Among the nonionic surfactants which may be employed by themselves or mixed, there may be mentioned in particular: polyethoxylated, polypropoxylated or polyglycerolated alcohols, alkylphenols and fatty acids containing a fatty chain containing from 8 to 18 carbon atoms. There may also be mentioned copolymers of ethylene propylene oxides, ethylene oxide and propylene oxide condensates with fatty alcohols, polyethoxylated fatty amides, polyethoxylated fatty amines, ethanolamides, glycol fatty acid esters, sorbitan fatty acid esters which are oxyethylenated or otherwise, sucrose fatty acid esters, polyethylene glycol fatty acid esters, phosphoric triesters, and fatty acid esters of glucose derivatives.

Other compounds forming part of this class are: the products of condensation of a monoalcohol, an α-diol, an alkylphenol, an amide or a diglycolamide with glycidol or a glycidol precursor such as:

$$R_4-CHOH-CH_2-O-(CH_2-CHOH-CH_2-O)_p-H$$

in which $R_4$ denotes an aliphatic, alicyclic or arylaliphatic radical preferably containing from 7 to 21 carbon atoms and their mixtures, the aliphatic chains being capable of containing ether, thioether or hydroxymethylene groups and in which p is from 1 to 10 inclusive, such as described in French Patent 2,091,516. Also useful are compounds corresponding to the formula:

$$R_5O\text{-}[C_2H_3O\text{-}(CH_2OH)]_q\text{-}H$$

in which $R_5$ denotes an alkyl, alkenyl or alkylaryl radical and q has a statistical value from 1 to 10 inclusive, such as described in French Patent 1,477,048 and compounds corresponding to the formula:

$$R_6\text{-}CONH\text{-}CH_2\text{-}CH_2O\text{-}CH_2\text{-}CH_2\text{-}O\\ \text{-}(CH_2\text{-}CHOH\text{-}CH_2\text{-}O)_r\text{-}H$$

in which $R_6$ denotes a radical or a mixture of straight-chain or branched, saturated or unsaturated aliphatic radicals which may optionally contain one or more hydroxyl group(s), containing from 8 to 30 carbon atoms, of natural or synthetic origin, r denotes an integer or decimal number from 1 to 5 and denotes the average degree of condensation, such as are described in French Patent 2,378,763.

The nonionic emulsions consist principally of a mixture of oil and/or a fatty alcohol, or polyethoxylated or polyglycerolated alcohols such as polyethoxylated stearyl or ceteraryl alcohols.

The anionic emulsions preferably consist of amine stearates.

In addition to the above-mentioned components, the compositions according to the present invention may contain ingredients which are conventionally employed, especially in make-up compositions, and are chosen from emollients, preserving agents, sequestering agents, perfumes, thickeners, oils, silicones, cohesion agents, polymers, as well as alkalifying or acidifying agents which are usually employed in the field of cosmetics.

The thickeners which can be employed may be natural or synthetic. Among natural thickeners, there may be mentioned gums of various kinds such as gum arabic, guar gum or carob gum. Among synthetic thickeners there may be mentioned cellulose derivatives such as hydroxyethylcellulose, carboxymethylcellulose, starch derivatives, cellulose ether derivatives containing quaternary ammonium groups, cationic polysaccharides, acrylic or methacrylic polymer salts, polyenes or polysiloxanes.

Thickening of the compositions may also be produced by a mixture of polyethylene glycol and polyethylene glycol stearate and/or distearate or by a mixture of phosphoric esters and fatty amides.

To make the subject of the invention better understood, a description will be given hereinafter, by way of purely illustrative examples which do not imply a limitation, of several methods of use.

EXAMPLE 1

1st step: Extraction of keratin from chicken feathers 100 g of previously washed chicken feathers, 2.1 liters of dimethylformamide and 860 ml of water are placed in a 4-liter reactor. The mixture is heated under reflux for 8 hours and then filtered hot. The filtrate is diluted with 15 liters of water. The precipitate obtained is separated off by filtration. The protein obtained in this way contains from 60 to 80% of water.

Comparative analysis of the amino acids indicates similar contents of amino acids in the untreated feathers, on the one hand and in the extracted protein, on the other hand. In both cases, the proportion of cystine is in the region of 7 (from 6.5 to 7.5 depending on the starting material).

2nd step: Preparation of a keratin derivative of formula (I), in which formula $M^+$ denotes $H^+$, and K denotes the keratin residue extracted from chicken feathers 350 g of moist keratin containing 30% of active substance and obtained in the first step, and 750 ml of acetic acid are placed in a 2-liter reactor. The whole is homogenized by stirring and a mixture of 375 ml of 110-volume hydrogen peroxide and of 1,125 ml of acetic acid is added over a period of approximately 40 min., while cooling with an ice bath. The reaction mixture is allowed to return to ambient temperature and is kept stirred for approximately 15 hours.

The mixture is then diluted with 5 liters of water. A precipitate is obtained which is filtered off and dried by freeze-drying. 70 g of the required keratin derivative are obtained in this manner in the form of a white powder.

The quantity of amino acids present in the keratin derivative obtained in this manner was determined. The results of this analysis are reported in the Table which follows, in which the values shown are expressed in grams of each amine acid per 100 g of protein matter.

Cysteic acid: 7.9
Cysteine: 0
Aspartic acid: 4.9
Threonine: 5.6
Serine: 13.7
Glutamic acid: 10.8
Proline: 11.1
Lanthonine: 0
Glycine: 6.8
Alanine: 4.3
Cystine: 0.2
Valine: 8.1
Methionine: 0
Isoleucine: 5.0
Leucine: 7.5
Tyrosine: 1.5
Phenylalanine: 5.3
Lysine: 1.4
Histidine: 0.5
Arginine: 5.4

The free amino acid and oligopeptide content is less than 0.1%.

EXAMPLE 2

The dry mascara composition which is formulated as follows is prepared:
Carnauba wax: 5 g
Candellila wax: 5 g
Ethyl alcohol: 3 g
Montmorillonite modified with an organic substance: 4 g
Compound of Example 1: 2 g
Talc: 10 g
Black iron oxide: 10 g
Isoparaffin, sufficient amount for: 100 g
The procedure is as follows:
The waxes are heated to 80° C. The talc and the pigments are added. The montmorillonite which has been modified with an organic substance and a part of the isoparaffin are then incorporated. At about 40° C., the compound of Example 1, ethyl alcohol and the remainder of the isoparaffin are added. The whole is passed through a grinder.

After a very short application time this mascara produces good make-up by sheathing the eyelashes and increasing the length of the eyelashes.

Examples 3 to 8 which follow refer to mascara compositions in emulsion form. These mascaras are ready for use. The general procedure is as follows:

The waxes are melted. The pigments are incorporated. The aqueous phase containing, depending on the case, the gums and/or the hydroxyethylcellulose and the compound of Example 1 is heated to the same temperature as the wax phase. The two phases are mixed and stirred vigorously.

The mascaras produced in this manner, the formulations of which are given below, require relatively short application times and nevertheless result in good make-up.

EXAMPLE 3

The mascara composition formulated as follows is prepared:
  Triethanolamine stearate: 15 g
  Beeswax: 8 g
  Paraffin: 3 g
  Rosin: 2 g
  Ozokerite: 10 g
  Propyl para-hydroxybenzoate: 0.20 g
  Methyl para-hydroxybenzoate: 0.20 g
  Gum arabic: 0.50 g
  Compound of Example 1: 1 g
  Black iron oxide: 5 g
  Aluminosilicate polysulphide: 5 g
  Water, sufficient amount for: 100 g

EXAMPLE 4

The mascara composition which is formulated as follows is prepared:
  2-amino-2-methyl-1-propanol stearate: 2 g
  Candelilla wax: 5 g
  Beeswax: 8 g
  Methyl para-hydroxybenzoate: 0.15 g
  Propyl para-hydroxybenzoate: 0.15 g
  Carob gum: 3 g
  Xanthane gum: 3 g
  Compound of Example 1: 0.50 g
  Black iron oxide: 8 g
  Water, sufficient amount for: 100 g

EXAMPLE 5

The mascara composition which is formulated as follows is prepared:
  Triethanolamine stearate: 20 g
  Microcrystalline wax: 5 g
  Carnauba wax: 10 g
  Beeswax: 3 g
  Imidazolidinylurea: 0.30 g
  Propyl para-hydroxybenzoate: 0.15 g
  Tragacanth gum: 5 g
  Black iron oxide: 5 g
  Water, sufficient amount for: 100 g

EXAMPLE 6

The mascara composition which is formulated as follows is prepared:
  Triethanolamine stearate: 15 g
  Candelilla wax: 8 g
  Carnauba wax: 10 g
  Hydroxyethylcellulose: 1 g
  Compound of Example 1: 5 g
  Black iron oxide, 8 g
  Methyl para-hydroxybenzoate: 0.15 g
  Propyl para-hydroxybenzoate: 0.15 g
  Water, sufficient amount for: 100 g

EXAMPLE 7

The mascara composition which is formulated as follows is prepared:
  Triethanolamine stearate: 10 g
  Candelilla wax: 15 g
  Beeswax: 17 g
  Xanthane gum: 1 g
  Compound of Example 1: 1 g
  Black iron oxide: 5 g
  Aluminosilicate polysulphide (ultramarine blue): 0.4 g
  Preserving agent, sufficient amount Water, sufficient amount for: 100 g

EXAMPLE 8

The mascara composition which is formulated as follows is prepared:
  Triethanolamine stearate: 10 g
  Carnauba wax: 8 g
  Beeswax: 8 g
  Compound of Example 1: 6 g
  Black iron oxide: 5 g
  Aluminosilicate polysulphide: 4 g
  Preserving agent, sufficient amount Water, sufficient amount for: 100 g

EXAMPLE 9

A dry mascara block with the following formulation is prepared:
  Triethanolamine stearate: 25 g
  Beeswax: 6 g
  Microcrystalline wax: 22 g
  Saturated fatty acid glycerides: 11 g
  Methyl para-hydroxybenzoate: 0.15 g
  Propyl para-hydroxybenzoate: 0.15 g
  Gum arabic: 5.70 g
  Compound of Example 1: 1.50 g
  Red iron oxide: 5 g
  Black iron oxide: 5 g The procedure is as follows:

The waxes are melted. The pigments are added. The gum arabic and the compound of Example 1 are incorporated. The mixture is passed through a heated grinder. The remaining ingredients are added. The whole is melted again and cast in molds with gentle stirring.

Good eyelash make-up is obtained after a very short application time.

An example demonstrating the marked lengthening of the eyelashes which is produced by the make-up compositions according to the invention will be given below.

EXAMPLE 10

Compositions which conform to the above-mentioned Examples 3 and 8 respectively, on the one hand and, compositions which conform to these two examples, except that they do not include the compound of Example 1, on the other hand, are prepared.

Each of these four compositions is applied with a brush to ten sable-hair paint brushes, each application requiring ten brush strokes over the paintbrush. The length of each paintbrush is measured before and after application of the composition by means of a binocular magnifier with a magnification of 7.94 and the elongation of the paintbrush is determined. The average of the ten elongations measured for each of the compositions is taken. The results, expressed in micrometer units at a magnification of 7.94, are reported in the following table:

TABLE

|  | Composition of Example 3 | Composition of Example 8 |
|---|---|---|
| without compound of Example 1 | 2 | 0.8 |
| with compound of Example 1 | 4.7 | 5.7 |

The very clear superiority of the compositions according to the invention in respect of producing a lengthening of the eyelashes can be seen.

What is claimed is:

1. A mascara composition comprising in a cosmetically acceptable carrier at least one wax, and at least one keratin derivative having the formula

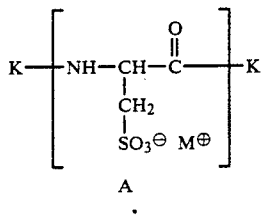

(I)

wherein
K is a keratin residue,
$M^\oplus$ is hydrogen, a cation derived from an alkali metal or magnesium, or $N^\oplus R_4$ wherein the R radicals are identical or different and represent hydrogen, alkyl containing 1-4 carbon atoms or hydroxyalkyl containing 1-4 carbon atoms, the unit A represents from 3 to 15 weight percent of said keratin and the protein chain of the keratin being modified only by said unit A.

2. The composition of claim 1 wherein the keratin residue K originates from a material selected from the group consisting of hair, wool, hoof, horn, fur, skin, silk or feather.

3. The composition of claim 1 wherein the keratin derivative of formula (I) has a molecular weight ranging from $10^4$ to $10^5$.

4. The composition of claim 1 wherein said keratin derivative of formula (I) is present in an amount ranging from 0.1 to 40 weight percent based on the total weight of said composition.

5. The composition of claim 1 wherein said wax is present in an amount ranging from 2 to 40 weight percent based on the total weight of said composition.

6. The composition of claim 1 wherein the weight ratio of said keratin derivatives to said wax ranges form 0.01:1 to 1:1.

7. The composition of claim 1 in the form of a water-in-oil emulsion, an oil-in-water emulsion, a suspension in a solvent medium, in dry solid form or in paste form.

8. The composition of claim 1 which also includes a surface-active agent present in an amount ranging from 2 to 30 weight percent based on the total weight of said composition.

9. The composition of claim 1 which also includes, as an adjuvant, at least one of an emollient, a preservative, a sequestering agent, a perfume, a thickener, an oil, silicone, a cohesion agent or polymer, an alkalizing agent or an acidifying agent.

10. The composition of claim 1 in the form of a water-in-oil emulsion.

11. The composition of claim 1 in the form of an oil-in-water emulsion.

12. The composition of claim 1 in the form of a suspension in a solvent medium.

13. The composition of claim 1 in dry, solid form.

14. The composition of claim 1 in paste form.

15. The composition of claim 1 wherein said wax has a melting point ranging form 60° to 110° C. and a needle penetration, expressed in tenths of a millimeter as measured in accordance with ASTM D5 and NFT 004 standards, ranging from 3 to 40 at 25° C..

16. The composition of claim 15, wherein said wax is selected from the group consisting of an animal wax, a plant wax, a mineral wax and a synthetic wax.

17. The composition of claim 16 wherein said animal wax is selected from the group consisting of beeswax, lanolin wax and Chinese insect wax.

18. The composition of claim 16 wherein said plant wax is selected from the group consisting of carnauba wax, candelilla wax, ouricury wax, cork fiber wax, sugar cane wax and Japan wax.

19. The composition of claim 16 wherein said mineral wax is selected from the group consisting of paraffin wax, microcrystalline wax, montan wax and ozokerite.

20. The composition of claim 16 wherein said synthetic wax is selected from the group consisting of polyethylene wax, wax produced by Fischer-Tropsch synthesis, waxy copolymer and esters thereof.

21. The composition of claim 1 which also includes at least one of an inorganic pigment, an organic pigment, a Cochineal Carmine-based lake, a pearlescent pigment or a colored pearlescent pigment.

22. The composition of claim 21 wherein said inorganic pigment is titanium dioxide, an optionally surface treated black, yellow, red or brown iron oxide, manganese violet, ultramarine blue, chromium oxide, chromium hydrate or ferric blue.

23. The composition of claim 21 wherein said organic pigment is D&C Red No. 19, D&C Red No. 9, D&C Red No. 21, D&C Orange No. 4, D&C Orange No. 5, D&C Red No. 27, D&C Red No. 13, D&C Red No. 7, D&C Red No. 6, D&C Yellow No. 5, D&C Red No. 36, D&C Orange No. 10, D&C Yellow No. 6, D&C Red No. 30 or D&C Red No. 3.

24. The composition of claim 21 wherein said colored pearlescent pigment is titanium mica with iron oxide, titanium mica with ferric blue or chromium oxide, titanium mica with an organic pigment or bismuth oxychloride.

25. The composition of claim 21 wherein said pigment is present in an amount ranging from 3 to 20 weight percent based on the total weight of said composition.

26. The composition of claim 21 wherein said pearlescent pigment is a white pearlescent pigment.

27. The composition of claim 26 wherein said white pearlescent pigment is mica coated with titanium oxide or bismuth oxychloride.

* * * * *